United States Patent [19]

Mikhailovich et al.

[11] Patent Number: 5,600,240
[45] Date of Patent: Feb. 4, 1997

[54] STRUCTURE FOR A CYLINDRICAL EDDY-CURRENT PROBE HAVING A HOLLOW BODY CONTAINING AN ELASTIC SUBSTRATE WITH AXIALLY ALIGNED SENSOR COILS

[75] Inventors: Ulitin Y. Mikhailovich; Gorskaya L. Evgenevna, both of Moscow, Russian Federation

[73] Assignee: Intron Plus, Ltd., Moscow, Russian Federation

[21] Appl. No.: 356,317

[22] PCT Filed: Apr. 28, 1994

[86] PCT No.: PCT/RU94/00095

§ 371 Date: Dec. 28, 1994

§ 102(e) Date: Dec. 28, 1994

[87] PCT Pub. No.: WO94/25866

PCT Pub. Date: Nov. 10, 1994

[30] Foreign Application Priority Data

Apr. 29, 1993 [RU] Russian Federation ............. 93025817

[51] Int. Cl.⁶ .................................................. G01N 27/90
[52] U.S. Cl. ...................... 324/219; 324/234; 324/239; 324/262; 336/200
[58] Field of Search ...................... 324/219–221, 324/228, 234, 236–238, 239–243, 260–262; 336/200, 208, 232, 233, 234

[56] References Cited

U.S. PATENT DOCUMENTS

| | | | |
|---|---|---|---|
| 3,035,353 | 5/1962 | Hovemeyer et al. | 324/219 X |
| 3,504,276 | 3/1970 | Proctor et al. | 324/260 |
| 3,723,861 | 3/1973 | Samples | 324/237 |
| 3,840,802 | 10/1974 | Anthony | 324/219 |
| 3,940,689 | 2/1976 | Johnson, Jr. | 324/221 |
| 3,988,665 | 10/1976 | Neumaier et al. | 324/240 |
| 4,072,895 | 2/1978 | Rogachev et al. | 324/238 |
| 4,107,605 | 8/1978 | Hudgell | 324/220 |
| 4,292,589 | 9/1981 | Bonner | 324/221 |
| 4,303,884 | 12/1981 | Malick | 324/220 |
| 4,480,225 | 10/1984 | Nance et al. | 324/220 X |
| 5,023,549 | 6/1991 | Dau et al. | 324/220 |

FOREIGN PATENT DOCUMENTS

| | | | |
|---|---|---|---|
| 3050497 | 8/1988 | Germany. | |
| 0741140 | 6/1980 | U.S.S.R. | 324/219 |

*Primary Examiner*—Sandra L. O'Shea
*Assistant Examiner*—Jay M. Patidar
*Attorney, Agent, or Firm*—Jones, Tullar & Cooper, P.C.

[57] ABSTRACT

A structure for a small and durable eddy-current probe for testing of conductive tubes, pipes and apertures in work pieces such as vias in printed circuit boards. A thin, rectangular elastic dielectric printed circuit substrate has sensor conductor loops printed on one side. That dielectric printed circuit substrate is placed on a thin rectangular steel sheet (the probe body) and the substrate and body are rolled into a strong, unitary eddy current probe structure which has the sensor loops 3 safely protected on the interior of the rolled-up probe body 1. The steel probe body cylinder thus formed has an external diameter D and an internal diameter d. The ratio of D/d is, preferably, in a range of 1.4 to 1.6. Bonding pad sites 5 are formed on the elastic substrate, for making electrical connections to the probe. The probe interior may be filled with magnetically conductive material.

7 Claims, 4 Drawing Sheets

STRUCTURE FOR A CYLINDRICAL EDDY-CURRENT PROBE HAVING A HOLLOW BODY CONTAINING AN ELASTIC SUBSTRATE WITH AXIALLY ALIGNED SENSOR COILS

THE BACKGROUND

The present invention relates to the non-destructive testing of workpiece properties and, in particular, to eddy-current probes for the non-destructive testing of pipes and holes of a small diameter, such as testing the coating in the through-holes of printed circuit boards.

Normally holes of printed circuit boards vary in diameter from 0.5 to 2.0 mm, whereas thickness of coating in through-holes varies from 15 to 50 microns. The material of electroplating is usually copper. There is not much prior art for testing within apertures of such small dimensions.

It is known in the art to use an eddy-current probe for non-destructive testing of electrically conductive plating in holes of printed circuit boards. Prior art probes used an oblong cylindrical core featuring excitation and measuring coils enveloping said core, whose wires are stretched along the axis of said core (U.S. Pat. No. 4,072,895, ). The known method for manufacturing said probe consists of winding an insulated wire on the cylindrical body as its coil (see, for example Reference Manual Non-destructive Testing, edited by R. McMaster, tr. from English, part 2, Moscow, Energy Publishers, 1965).

In the prior art the conductors of the coils envelop the cylindrical core and intersect at the butts or ends of the core. Winding such conductors is a delicate job due to minute dimensions of the core (less than 1 mm). Manual winding is usually performed with the aid of a microscope and so electrical characteristics of the prior art probes vary considerably. Moreover, conductors of the probe coils may be easily damaged when the probe is inserted into a hole to be tested.

Also known in the art is an eddy-current probe which is not so easily damaged (see, for example, German Patent No. 3,050,497, 1982). This probe is intended for non-destructive testing of metal coatings in the pipes and holes in the workpieces, and comprises a carrying cylindrical core and a enveloping coil whose wires are stretched along the axis of the core. All the wires are secured on in the lateral surface of the core. Said coil carries a special coating to be protected from mechanical damage.

Moreover, said patent describes the method of manufacturing for such probes including manufacturing of the flat elastic substrate made of dielectric material with dimensions chosen according to the core size, forming the coil and securing of the formed coil on the surface of the core. The coil forming may be made through, for example, photolithography or laser processing of the pre-metallized surface.

This method gives some advantages: small dimensions, technologically-based design, high sensitivity, and a probe output which is invariant to changes in the radial and axial placement of the probe with respect to the axis of the hole under test. But during the application this probe has insufficient mechanical stability and may suffer from a short life time for the coil's protective coating. The low durability of this probe is the result of the high core length-to-diameter ratio. Since the probe's outside diameter is, at the limit, diameter defined according to the holes to be tested, the protective coating's enlargement results in the reducing of the carrying core's diameter, and so, diminishes the mechanical durability of the probe.

This problem becomes acute during the testing of coatings in through holes or vias in printed circuit boards. In such testing one encounters sharp edges within the through holes. This probe is liklely to encounter multiple mechanical influences and yet is limited in core size to approximately 0.5 mm.

SUMMARY OF THE INVENTION

An object to the invention is the solution of the problem of increasing the probe is mechanical stability and resistance to damage without enlarging the probe's cross-sectional dimensions.

According to the first aspect of the invention, there is provided an eddy-current probe for non-destructive testing of holes in workpieces and pipes, comprising an axial elongated axial-symmetrical body and coils, having its conductors arranged parallel to the body axis, the conductor of each coil being joined together to form a spiral carried on and in the plane of the lateral surface of the body. Spiral coils end with bonded pads connected to the external leads. Increased the mechanical durability for the probe is provided through use of a hollow body with a selected ratio of external and internal diameters. This ratio, D/d is defined from the transverse dimensions of the external diameter D and the internal diameter d and is preferably in a range of 1.4 to 1.6. The coils on the elastic substrate are secured to an internal surface of the probe's body.

The cross sectional area of the probe's body with ratio D/d=1.4 approximately equals the cross sectional area of a solid body of d transverse dimension. However, due to the tube-like shape, the probe's body is more mechanically stable than the solid one having the equal cross sectional area. Since the coils are secured within the probe body, they are less likely to be damaged when the probe is used. This arrangement eliminates the requirement for protective coatings on coils; for this invention, the mechanical stability of the probe is provided through increasing the thickness of body wall but not the external dimensions of the body.

A significant increase in body wall thickness will tend to reduce the probe's sensitivity. According to the findings of the applicant's special research, a metal probe's body can have a selected ratio D/d as high as 1.6 without significantly diminishing the probe's sensitivity. Any further increase in this ration will (for a given probe external D) yield a corresponding decrease in the internal diameter d, which will adversely impact coil performance.

In the structure of the present invention, bonding pads with holes are fabricated on an elastic substrate along with the coils discussed above. These bonding pads are electrically connected to the coils and facilitate wiring of the probe. The probe's body is tubular or cylindrical and has an internal cavity which may be filled with a magnetically conductive material. The probe's body fits within and is supported by a holder. The central core may have a first threaded end which is threaded in the body and may be fastened (within the body) to the holder with a hardening adhesive. The second end of the central core is a conical tip, thus the end of the probe is preferably plugged with a conical tip.

The tubular probe body is fastened to the holder. The holder has a first side and a second side and has an aperture which runs through the holder from the first side to the second side. The probe body is inserted in the aperture at the first side. The tip of body is pushed through the holder and out the second side, and an end of the probe body, opposite the tip, remains extended from the first side. That probe end is cut into lobes which are bent down at a 90 degree angle to the probe body central axis and those lobes are then fastened to the first side of the holder.

The method for manufacturing the probe of the present invention includes forming the coils on a planar dielectric elastic substrate, securing the substrate to the planar flat reaming of the metallic body, and rolling the substrate and body into the cylindrical shape of the probe.

BRIEF DESCRIPTION OF THE DRAWINGS

The following figures are illustrative of the preferred embodiments the probe and do not cover all of the possible variants. The present invention is illustrated in the following figures, in which.

DETAILED DESCRIPTION OF THE PREFERRED EMBODIMENT

According to the above, one of the main problems to be solved is the testing of the coating in the through-holes of printed circuit boards, so this particular case is under consideration as an example.

The eddy-current probe combines the body 1 which is formed as a hollow tube with D for an external diameter, D is selected according to the diameter of holes to be tested (i.e., D=0.8 mm). The internal diameter d is defined from the ratio $1.4 < D/d < 1.6$. If D=0.8 mm, dimension d may vary from 0.5 to 0.57 mm. For smaller values of diameter D the value of diameter d should be chosen closer to the upper limit, and the d values, close to the lower limit, should correspond to the bigger values of D. The tests on bending show the probe fabricated in accordance with the above recommended D/d ratio is more reliable and mechanically stable than the prototype one for the holes of the same diameters in printed circuit boards. The probe sensitivity is acceptable and not influenced by the body, which is made of steel.

Figure 1:
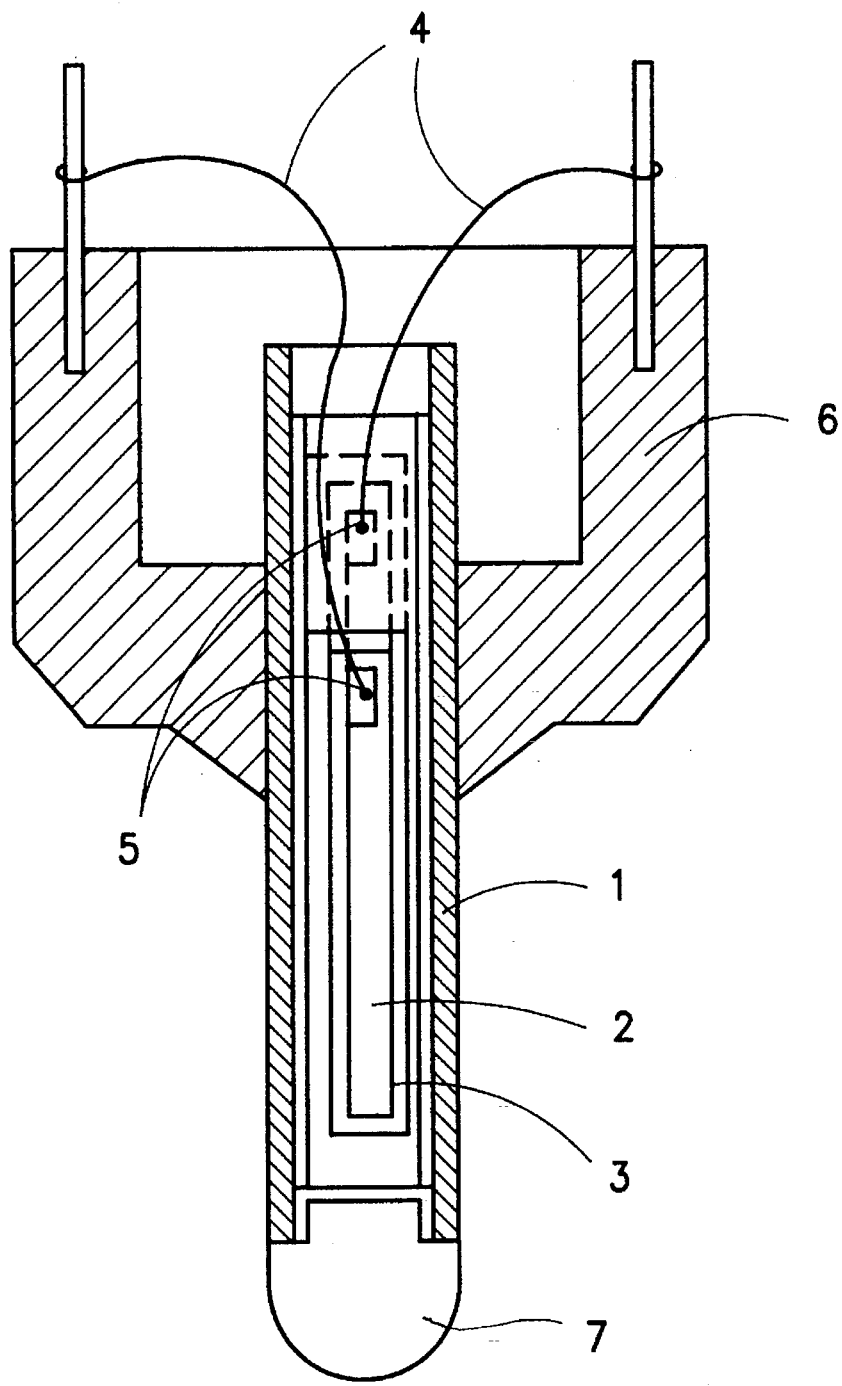
FIG. 1 illustrates the longitudinal section of the probe.

On the internal surface of the body 1 there is a dielectric elastic substrate 2 upon which are formed spiraled coils 3. The coils are extended along the axis of the body 1. The substrate and the coils correspondingly may be formed in one or several layers and consist of a few sections placed symmetrically. The bonding pads 5 are formed on the substrate 2 at the same time with the coils 3 and are connected to the wire leads 4 as shown in FIG. 1, after the coils are formed. The body 1 is then fastened to the holder 6. The bottom or second side of the holder 6 is the operative side of the holder, adjacent to the working end of the probe's body, and is tapered into a cone-like shape to provide an easy way to center the probe in the hole under test. The end of the probe's body is closed with a plug having a tip which has a hemispherical shape or a rounded cone shape. The internal cavity of the body may be filled up with any magnetically conductive material, such as one with f.e ferromagnetic elements distributed in a fast-hardening compound.

Figure 2:
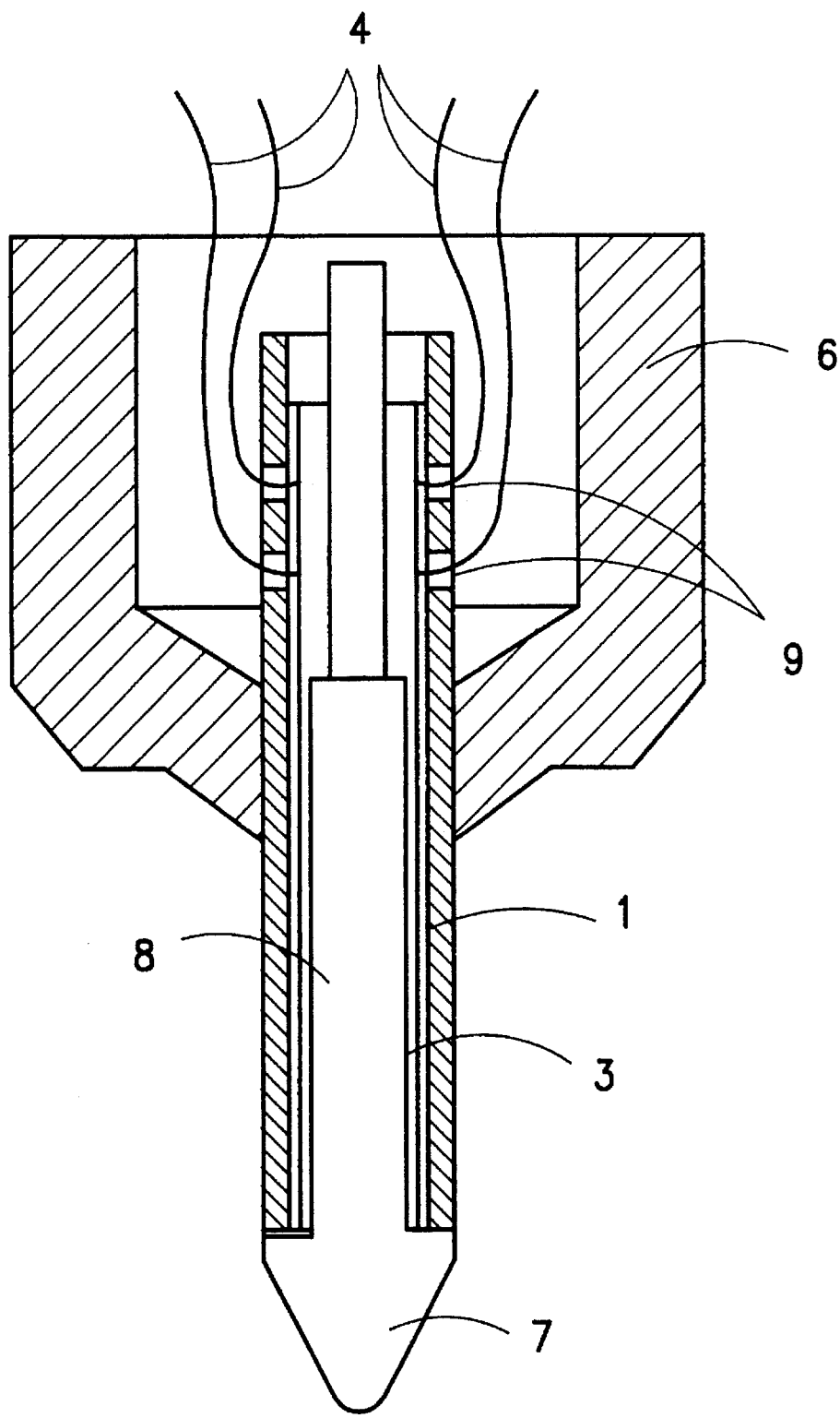
FIG. 2 illustrates the probe with the central core inserted.

The core 8 closed with cone plug 7 may be mounted inside the body 1 with the coils 3 (see FIG. 2). In this case the portion of the core 8 inserted into the holder may be formed as a rolled up cylinder (a spiral in cross section), these are easily formed with cores of a small diameter. The spiral part of the core is fastened with the hardening compound to provide the tight mounting of the body 1 in the holder 6.

In the preferred embodiment the external wire leads 4 connected to the bonding pads 5 may be brought out to the external surface of the body 1 (see FIG. 2). In this case special holes 9 are made in the body 1 close to the location of the bonding pads 5. The holes 9 may be metallized and electrically connected to the pads 5. While the body 1 is made of the electrically conductive material, the dielectric layer is situated between the surface of the body and the metallizing layer with the proper thickness to provide the reliable insulation. The input/output contacts of the probe are usually placed on the butt of the holder.

Figure 3:
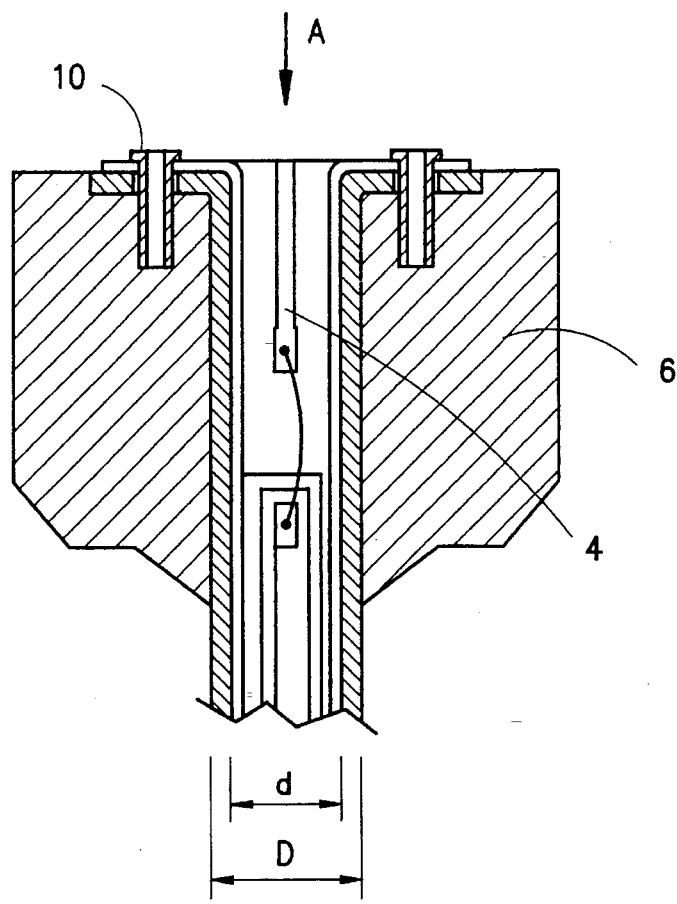
FIGS. 3 and 4 illustrate the probe with the body coming out of the other face of the holder.
Figure 4:
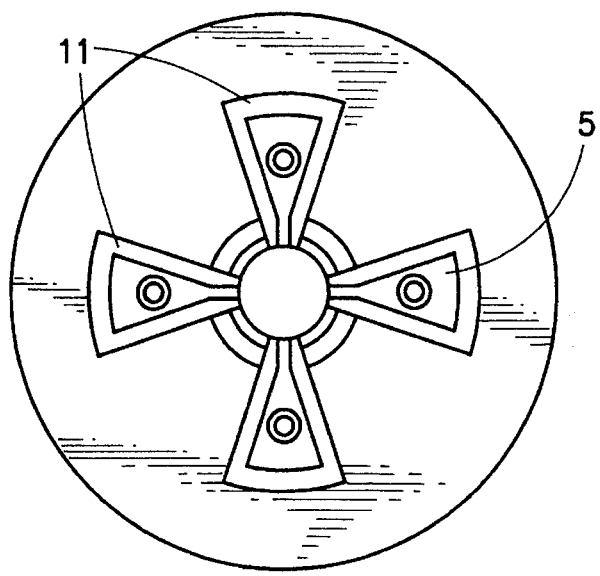

The preferred embodiment for the contacts is presented in FIG. 3. The body 1 comes out of the holder 6. The outcoming portion of the body 1 is cut to form lobes 11. To provide the mechanical stability the body 1 is made of steel and the dielectrical elastic substrate 2 is situated on the out-coming portion of the body 1 also, to provide the proper insulation of the wire leads 4 from the body 1. The lobes 11 are bent and fastened close to the input/output contacts 10. The contacts 10 may be embedded into the face of the holder 6.

Figure 5:
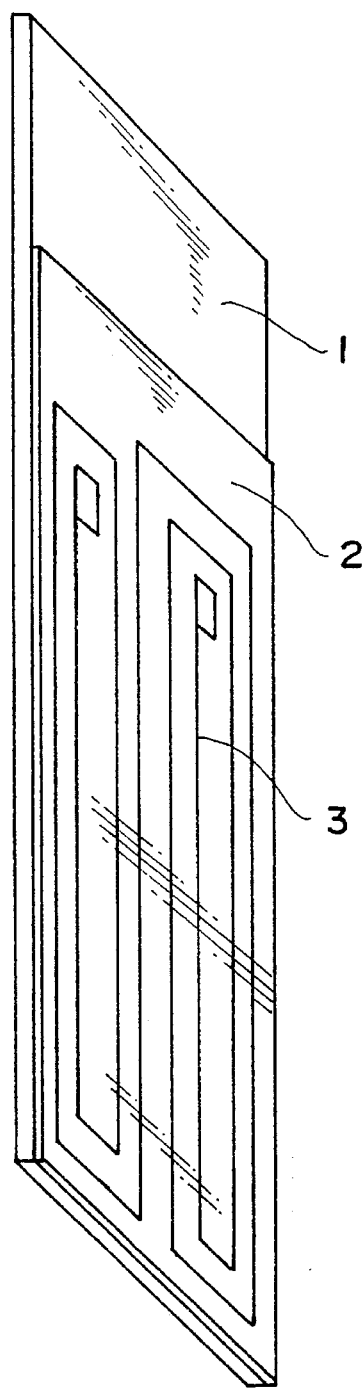
FIG. 5 illustrates the stage of the probe manufacturing before the body is formed.

The probe proposed is manufactured as follows:

A flat reaming is made in accordance with the defined dimensions of the body 1; a reaming is defined as a rectangular planar part which one obtains by cutting a cylinder in a longitudinal direction and unrolling it. The height of the reaming equals the height of the body 1 and the width of the reaming equals the perimeter of the body 1. Apart from this the coils 3 are formed on the dielectric elastic substrate 2 by one of the known methods, i.e., thin-film evaporation. In case of multilayer coils 3 conductors of the first layer are plated with a dielectric layer, then the second layer conductors are formed and so on. The inter-layer connections are made through the pre-drilled holes with metal coating inside. The elastic substrate 2 carrying the coils 3 is put upon the flat rectangular planar part of the body 1 as shown in FIG. 5. Next, the probe body 1 is formed by rolling this "sandwich" into a cylinder of the defined diameter.

It is possible to form the coils 3 directly on the surface of the flat reaming of the body 1 by photolithography or laser processing. In this case the surface of the reaming is pre-metallized. If the body 1 is made of steel foil the reaming surface is coated with dielectic material before metallizing. After the coils are formed the flat reaming is formed into tube of a defined diameter.

The wire leads 4 may be formed at the same time with the coils 3 or connected to the bonding pads before the tube body is formed or connected from outside when the tube body 1 is already formed. The formed sensitive portion of the body is fastened in the holder 6. The external contacts are mounted.

The eddy-current probe operates in the following manner: The coils 3 of the probe are connected to, for example, the resonant circuit of the oscillator or to the bridge circuit which has one branch connected to the oscillator and the other to the measuring device or set (such tests sets are well known in the prior art). The probe is inserted into a hole under test in coaxial alignment; insertion is aided by the use of the cone plug tip.

An oscillating signal from the test set provides an alternating current in the coil 3. This creates an alternating magnetic field around the coil which excites an eddy current in the metal plating (or coating) within the hole under test, i.e. within the through hole of a printed circuit board. The test set oscillator is adjustable for frequency and a frequency is selected which will be most revealing of defects for given hole under test. For a given plating thickness, and a given set of axial or peripheral cracks within the plating, the resulting eddy current in the plating will vary. Thus, the magnetic field in the coil and the EMF excited as a result of the initiation of the measurement can be seen to vary with that eddy current. The probe of the present invention performs these functions while providing greater mechanical stability and greater protection from damage to the measuring coil. The alternating current through the coil 3 of the probe creates the mechanical damage.

Industrial Application

The invention may be applied in all the industries connected to the manufacturing and application of the printed circuit boards for non-destructive testing the coating in the through-holes, for measuring the geometric dimensions of the holes in metal sheets, profiles and so on, for measuring the characteristics of the electroconductive material for the coating in the holes and pipes (special electrical conductivity, magnet properties), for quality control the surfaces of the holes in workpieces and pipes, f.e, routines of the thermal and thermochemical processing, to discover the overheated areas while machining and so on.

We claim:

1. An eddy-current probe for non-destructive testing within holes in work pieces or within pipes, comprising:

a hollow cylindrical metallic body having an inner surface with an inner diameter d, an outer surface with an outer diameter D and a central axis;

an elastic dielectric substrate, within said hollow cylindrical metallic body, having an inner surface and an outer surface; said substrate outer surface juxtaposed with said metallic body inner surface;

a first conductor coil, fabricated onto said substrate inner surface, having a conductor arranged parallel to the body central axis; and the ratio D/d is in the range of 1.4 to 1.6.

2. The probe of claim 1, wherein said coils include bonding pad terminations which are connected to wire leads.

3. The probe as claimed in claim 1, further comprising:

magnetically conductive material disposed within said hollow cylindrical body.

4. The probe as claimed in claim 1, further comprising:

a central core mounted within said hollow body, said core having a first end and a second end, said second end terminating in a rounded conical tip.

5. A eddy-current probe of claim 4, wherein said central core within said body is affixed to a holder.

6. The probe of claim 1, further comprising:

a holder having a first top side, a second bottom side, and a cylindrical aperture which places the two sides in communication and is adpated to accept and support said metallic cylindrical body;

wherein a portion of the body is situated on the bottom side of the holder and the body goes through and comes out on the top side of the holder, said body further including lobes, said lobes being sent and fastened on the top side of the holder.

7. An eddy-current probe for non-destructive testing within holes in work pieces or within pipes, comprising:

a hollow cylindrical metallic body having an inner surface with an inner diameter d, an outer surface with an outer diameter D and a central axis;

an elastic dielectric substrate having an inner surface and an outer surface;

said substrate outer surface juxtaposed with said metallic body inner surface;

a first conductor coil, fabricated onto said substrate inner surface, having a conductor arranged parallel to the body central axis; and wherein a reaming of said metallic body, and said flexible substrate are rolled together to form a cylindrical probe structure having the ratio D/d in the range of 1.4 to 1.6.

* * * * *

UNITED STATES PATENT AND TRADEMARK OFFICE
CERTIFICATE OF CORRECTION

PATENT NO. : 5,600,240
DATED : February 4, 1997
INVENTOR(S) : ULITIN et al.

It is certified that error appears in the above-indentified patent and that said Letters Patent is hereby corrected as shown below:

TITLE PAGE:
Under item [19], change "Mikhailovich" to --Ulitin--.

In item "[75] Inventors", change "Ulitin Y. Mikhailovich" to --Yuri Mikhailovich Ulitin--.

Claim 6, line 9 thereof, change "sent" to --bent--.

Signed and Sealed this

Fifteenth Day of April, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   :   5,600,240
DATED        :   February 4, 1997
INVENTOR(S)  :   ULITIN et al.

It is certified that error appears in the above-indentified patent and that said Letters Patent is hereby corrected as shown below:

TITLE PAGE

In item "[75 Inventors]" change "Gorskaya L. Evgenievna" to

--Ludmila Evgenievna Gorskaya--.

Signed and Sealed this

Eighth Day of July, 1997

*Attest:*

BRUCE LEHMAN

*Attesting Officer*       Commissioner of Patents and Trademarks